United States Patent
Vought

Patent Number: 5,991,666
Date of Patent: *Nov. 23, 1999

[54] STERILE SURGICAL-THERMAL DRAPING SYSTEM AND METHOD

[75] Inventor: Kimber L. Vought, Columbus, Miss.

[73] Assignee: Microtek Medical, Inc., Columbus, Miss.

[*] Notice: This patent is subject to a terminal disclaimer.

[21] Appl. No.: 08/939,584

[22] Filed: Sep. 29, 1997

Related U.S. Application Data

[63] Continuation of application No. 08/620,931, Mar. 21, 1996, abandoned.

[51] Int. Cl.⁶ .................................................. A61F 7/00
[52] U.S. Cl. ........................... 607/98; 607/104; 607/114; 128/849; 128/854
[58] Field of Search ................................ 128/849–854; 607/96, 104, 108–112, 114; 126/204; 165/46

[56] References Cited

U.S. PATENT DOCUMENTS

| | | | |
|---|---|---|---|
| 4,736,088 | 4/1988 | Bart | 219/211 |
| 4,807,644 | 2/1989 | Sandhaus | 128/849 |
| 4,945,924 | 8/1990 | Poettgen | |
| 4,962,761 | 10/1990 | Golden | 607/104 |
| 5,025,777 | 6/1991 | Hardwick | 126/263 |
| 5,184,612 | 2/1993 | Augustine | 128/400 |
| 5,190,032 | 3/1993 | Zacoi | |
| 5,300,098 | 4/1994 | Philipot | 607/96 |
| 5,300,103 | 4/1994 | Stempel et al. | 607/108 |
| 5,304,213 | 4/1994 | Berke et al. | 607/104 |
| 5,350,417 | 9/1994 | Augustine | |
| 5,360,439 | 11/1994 | Dickerhoff et al. | 607/104 |
| 5,392,847 | 2/1995 | Stephenson | 165/46 |
| 5,405,371 | 4/1995 | Augustine et al. | 607/107 |
| 5,425,975 | 6/1995 | Koiso et al. | 428/74 |
| 5,800,483 | 9/1998 | Vought | 607/104 |

FOREIGN PATENT DOCUMENTS 8503216  8/1985  European Pat. Off.

Primary Examiner—Cary O'Connor
Assistant Examiner—Ryan Carter
Attorney, Agent, or Firm—Baker & Botts, L.L.P.

[57] ABSTRACT

A sterile surgical-thermal drape (10) is provided. The sterile surgical-thermal drape (10) includes a sterile surgical drape (12) that maintains a sterile field and a thermal device (14) attached (16) to the sterile surgical drape (12) for regulating the body temperature of a patient (32).

26 Claims, 5 Drawing Sheets

STERILE SURGICAL-THERMAL DRAPING SYSTEM AND METHOD

CROSS-REFERENCE TO RELATED APPLICATIONS

This application is a continuation of application Ser. No. 08/620,931, filed Mar. 21, 1996, entitled "Sterile Surgical-Thermal Draping System and Method," by Kimber L. Vought, now abandoned.

TECHNICAL FIELD OF THE INVENTION

This invention relates in general to the field of surgical drapes, and more particularly to a system and method for a sterile reusable or disposable surgical drape having thermo-regulatory/thermoprotective features.

BACKGROUND OF THE INVENTION

A patient under general anesthesia will undergo several physiological changes that inhibit the body's normal thermo-regulatory capabilities. General anesthesia depresses the function of thermoregulating centers in the hypothalamus, thus resulting in the body's inability to self-regulate body temperature. Infusion of intravenous fluid may contribute to cooling body temperature during surgery because such intravenous fluids absorb heat from the body when they are at a temperature below body temperature. Inspiration of dry anesthesia gases during surgery may also contribute to body temperature cooling during surgery because the dry gas both absorbs heat from the body and because of the cooling action created when water from the body is absorbed by the dry gas. Moreover, during surgery the body cavity may be exposed, which increases the effective surface area of the body and also cools body parts that are normally not exposed to the environment. The incidence of hypothermia occurring after surgery has been estimated to be as great as 60% to 90%.

To prevent hypothermia from occurring, it is necessary to provide active heating to a patient during surgery. One important requirement for any active heating system or method used during surgery is that it maintains a sterile surgical field. Another important requirement for any active heating system or method is that it delivers sufficient heat to the body to prevent the onset of hypothermia.

Although many devices exist that may be used to provide heat or to provide a sterile environment, none of these devices are capable of performing both functions simultaneously.

SUMMARY OF THE INVENTION

Therefore a need has arisen for a sterile surgical-thermal draping system and method that maintains a sterile field during surgery while providing heat to the patient in a manner that is sufficient to prevent the onset of hypothermia.

Accordingly, the present invention provides a sterile reusable or disposable surgical drape with thermo-regulatory/thermoprotective features that substantially eliminate or reduce the disadvantages and problems associated with previously developed surgical drapes and thermo-regulatory/thermoprotective devices.

One aspect of the present invention provides a sterile surgical-thermal drape. The sterile surgical-thermal drape includes a sterile surgical drape that maintains a sterile field and a thermal device attached to the sterile surgical drape for regulating the body temperature of a patient.

Another aspect of the present invention provides a method for packaging a sterile surgical-thermal drape. The packaging method includes attaching a sterile surgical drape to a flexible thermal device, folding the sterile surgical drape, and folding the flexible thermal device such that it encloses the sterile surgical drape.

Yet another aspect of the present invention provides a sterile surgical-thermal drape. The sterile surgical-thermal drape includes a sterile surgical drape that maintains a sterile field. The sterile surgical drape folds into a head section and a foot section. The sterile surgical-thermal drape also includes a flexible thermal device attached to the sterile surgical drape for regulating the body temperature of a patient. The thermal device folds into a head section and a foot section. A barrier attaches between the sterile surgical drape and the thermal device and encloses the sterile surgical drape to maintain the sterility of the sterile surgical drape. The sterile surgical drape may also include an incise or fenestration for exposing a portion of the patient's body.

Another aspect of the present invention is a sterile surgical-thermal drape that includes a sterile surgical surface and a thermal surface. The sterile surgical surface is used to maintain a sterile field. The thermal surface is connected to the sterile surgical surface, in such as manner as to form a compartment between the two surfaces.

The present invention provides several technical advantages. One important technical advantage of the present invention is that it provides a device that maintains a sterile surgical field while providing sufficient heat to prevent the onset of hypothermia in a patient. A device incorporating concepts of the present invention may be used to controllably provide heat to a patient under anesthesia while maintaining a sterile environment necessary to safely perform surgery.

Another important technical advantage of the present invention is that it provides a method for using a sterile surgical-thermal draping system that maintains the sterile qualities of the surgical-thermal draping system while allowing operating room personnel to handle and prepare the surgical-thermal draping system for use in surgery.

BRIEF DESCRIPTION OF THE DRAWINGS

For a more complete understanding of the present invention and the advantages thereof, reference is now made to the following description taken in conjunction with the accompanying drawings in which like reference numbers indicate like features and wherein.

DETAILED DESCRIPTION OF THE INVENTION

Preferred embodiments of the present invention are illustrated in the FIGURES, like numerals being used to refer to like and corresponding parts of the various drawings.

Figure 1A:
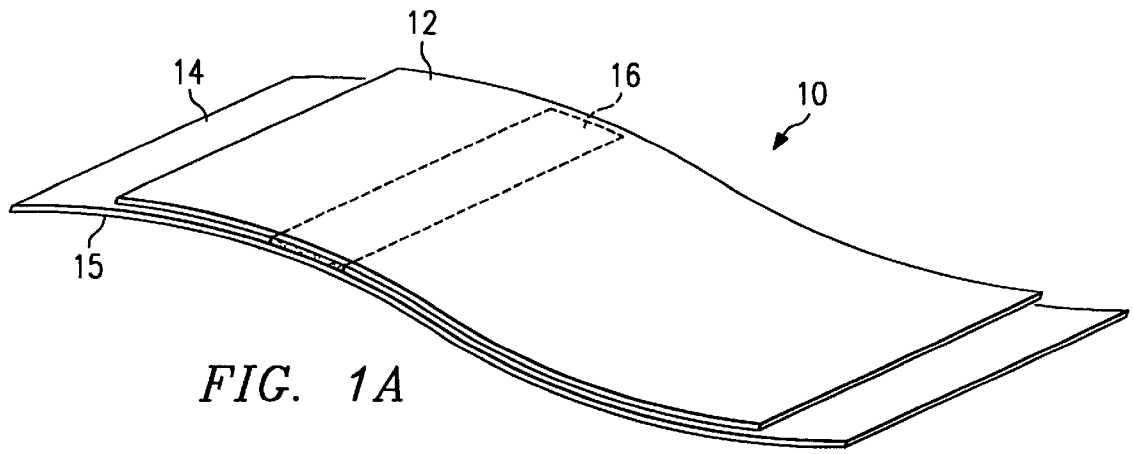
FIGS. 1A and 1B illustrate sterile surgical-thermal drapes embodying concepts of the present invention.

FIG. 1A shows sterile surgical-thermal drape 10 embodying concepts of the present invention. Drape 10 includes flexible sterile surgical drape 12 and flexible thermal device 14. Sterile surgical drape 12 and flexible thermal device 14 may be of identical size, or may have different shapes and sizes as shown in FIG. 1A. Sterile surgical drape 12 can be formed from many appropriate materials or combinations of materials, including, but not limited to, nonwoven materials, films, and woven materials. Flexible sterile surgical drape 12 is sterile, remains sterile, and is used to maintain a sterile field during surgery.

Flexible thermal device 14 may incorporate an active thermal heating or cooling device, but may also be a passive thermal barrier or insulator. Possible active thermal mediums that may be used in combination with flexible thermal device 14 include, but are not limited to, electrical heating elements, thermoelectric heating or cooling elements, hot or cold liquids, hot or cold gases, and endothermic or exothermic chemical reactants. In addition to an active thermal heating or cooling device, flexible thermal device 14 includes exterior surface 15 that contacts the patient when drape 10 is in use. Exterior surface 15 is typically a woven fabric, but may also be made from a nonwoven material or film.

Sterile surgical drape 12 and flexible thermal device 14 are connected at a predetermined location by connection 16. Connection 16 may be made by many appropriate fastening techniques, including, but not limited to, sonic welding, laser welding, adhesive attachment, heat sealing, hook and loop systems, plastic fixtures such as track bars or snaps, and zippers. In addition, connection 16 may be made by the material of sterile surgical drape 12 or flexible thermal device 14, such as by melting or softening the material. Connection 16 may be made at any desired location or locations, including but not limited to at a point, along a line or edge, or continuously at the interface between sterile surgical drape 12 and flexible thermal device 14. Connection 16 may also be used to form passageways for carrying a fluid (liquid or gaseous) between sterile surgical drape 12 and flexible thermal device 14, or a compartment for holding an electrical resistance heating element or manipulably rupturable compartment containing heat-generating or heat-absorbing reactants.

In operation, sterile surgical-thermal drape 10 is prepared for use by medical personnel, who first remove it from appropriate packaging and then place it on the desired patient surface with exterior surface 15 of flexible thermal device 14 in contact with the patient. Next, the appropriate connections are made between active heating or cooling equipment and flexible thermal device 14 so that device 14 provides appropriate heating or cooling. It should be noted that sterile surgical drape 12 is not in contact with any unsterilized surface or objects while connections to flexible thermal device 14 are made, thus maintaining the sterility of sterile surgical drape 12.

After all necessary connections have been made, sterile surgical-thermal drape 10 is positioned over a patient (not explicitly shown) with exterior surface 15 of flexible thermal device 14 in contact with the patient and sterile surgical drape 12 disposed outwardly from device 14. Surgical procedures may then be performed on exposed portions of the patient or through a fenestration in drape 10 (not explicitly shown) without risking inadvertent contamination of medical instruments or devices by contact with flexible thermal device 14. An incise may be used instead of a fenestration. An incise is typically a piece of translucent material that may be cut into a fenestration or opening of any desired size. For the purposes of the present invention, a fenestration or incise may be used interchangeably unless otherwise noted.

Figure 1B:
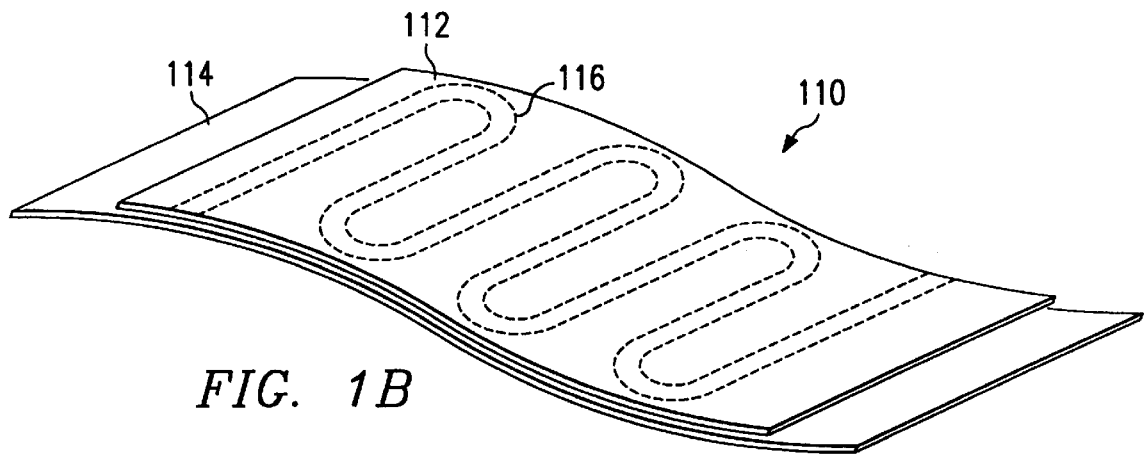

FIG. 1B shows sterile surgical-thermal drape 110 embodying concepts of the present invention. Drape 110 includes sterile surgical surface 112 and thermal surface 114, both of can be formed from many appropriate materials or combinations of materials, including, but not limited to, nonwoven materials, films, and woven materials. Sterile surgical surface 112 and flexible thermal surface 114 may be of identical size, or may have different shapes and sizes as shown in FIG. 1B. Drape 110 is sterile, remains sterile, and is used to maintain a sterile field during surgery.

Drape 110 incorporates an active thermal heating or cooling device or devices. Possible active thermal devices that may be used in combination with drape 110 include, but are not limited to, electrical heating elements, thermoelectric heating or cooling elements, hot or cold liquids, hot or cold gases, and endothermic or exothermic chemical reactants. As shown in FIG. 1B, passageways 116 are formed between sterile surgical surface 112 and thermal surface 114 by an appropriate method, such as by bonding, gluing, sonic welding, or melting the material of sterile surgical surface 112 or thermal surface 114. Instead of passageways, other thermal devices may be included between sterile surgical surface 112 and thermal surface 114, such as resistive heating elements or exothermic chemicals.

In operation, sterile surgical-thermal drape 110 is prepared for use by medical personnel, who first remove it from appropriate packaging and then place it on the desired patient surface with thermal surface 114 of drape 110 in contact with the patient. Next, the appropriate connections are made between active heating or cooling equipment and drape 110 so that drape 110 provides appropriate heating or cooling. It should be noted that sterile surgical surface 112 is not in contact with any unsterilized surface or objects while connections to drape 110 are made, thus maintaining the sterility of sterile surgical surface 112.

After all necessary connections have been made, drape 110 is positioned over a patient (not explicitly shown) with thermal surface 114 of drape 110 in contact with the patient and sterile surgical surface 112 disposed outwardly from drape 110. Surgical procedures may then be performed on exposed portions of the patient or through a fenestration in drape 110 (not explicitly shown) without risking inadvertent contamination of medical instruments or devices by contact with thermal surface 114.

One skilled in the art will recognize that sterile surgical-thermal drape 10 and drape 110 are exemplary. An embodiment of the present invention may incorporate features of either sterile surgical-thermal drape 10 or drape 110 in order to provide thermal regulatory capability during surgery while maintaining a sterile operating field.

Figure 2A:
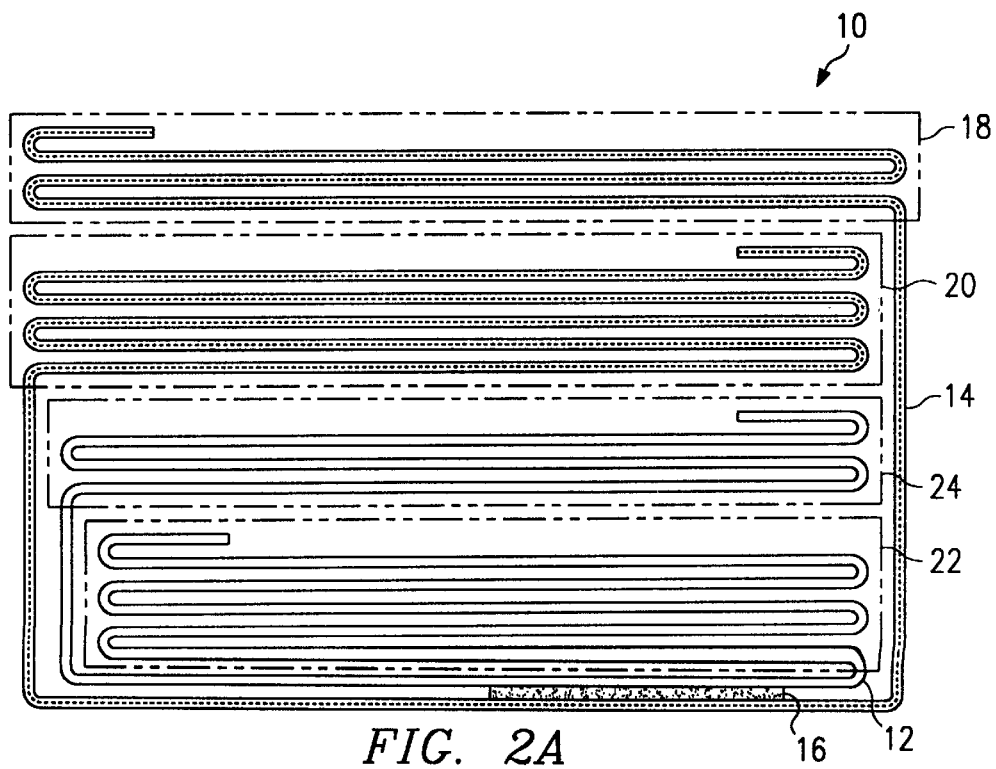
FIGS. 2A and 2B show sterile surgical-thermal drapes showing folding and attachments in accordance with the teachings of the present invention.

FIG. 2A illustrates sterile surgical-thermal drape 10 after folding, according to the teachings of the present invention. Thermal head section 18 and thermal feet section 20 are externally configured as shown. Surgical drape head section 22 and surgical drape feet section 24 are internally configured as shown, enclosed by flexible thermal device 14. This configuration of drape 10 allows sterile surgical drape 12 to be maintained in a sterile environment, and also provides access to flexible thermal device 14 so that it may be prepared for use, such as by attachment to an external heating or cooling system.

In operation, sterile surgical-thermal drape 10 is applied by first unfolding thermal device head section 18 and thermal device feet section 20. At this stage, sterile surgical drape 12 is still completely contained within a sterile environment. Because flexible thermal device 14 does not need to be maintained in a sterile environment, subsequent preparatory steps may be performed on device 14 after placing sterile surgical-thermal drape 10 on a non-sterile surface. Surgical drape head section 22 and surgical drape feet section 24 may then be unfolded and placed on top of thermal device head section 18 and thermal device feet section 20. Although the surface of sterile surgical drape 12 that is in contact with flexible thermal device 14 is no longer sterile, the opposite surface of sterile surgical drape 12 remains sterile. Sterile surgical-thermal drape 10 thus maintains a sterile field and allows for heating or cooling a patient.

Figure 2B:
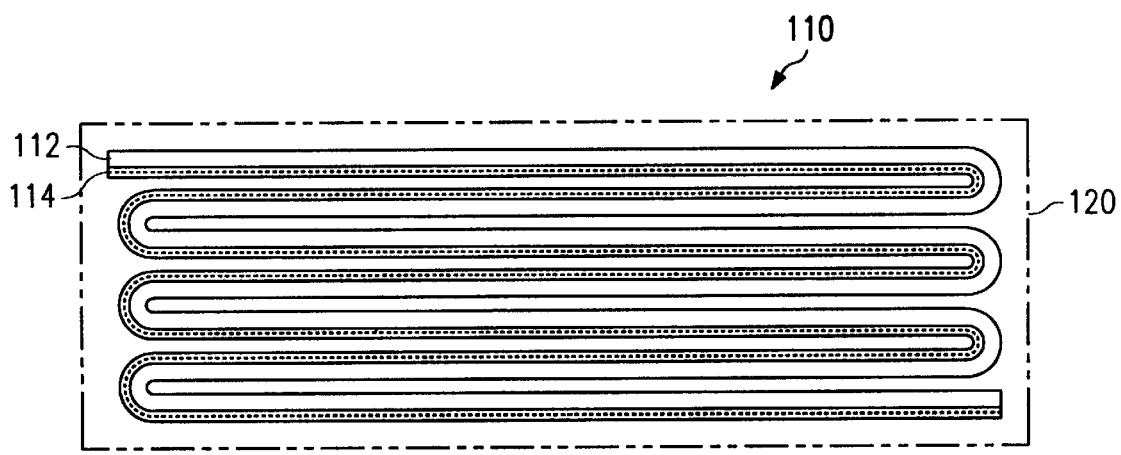

FIG. 2B illustrates drape 110 after folding, according to the teachings of the present invention. Drape 110 is contained within packaging 120. Because sterile surgical surface 112 and thermal surface 114 are coextensive with each other, all of drape 110 is sterilized and maintained within packaging 120. In operation, drape 110 is applied by opening packaging 120 and unfolding drape 110. At this stage, the sterility of sterile surgical surface 112 is maintained by placing drape 110 on thermal surface 114 while any preparatory steps are performed on drape 110. After drape 110 has been prepared, it is placed on the patient (not explicitly shown) with thermal surface 114 in contact with the patient and sterile surgical surface 112 facing the medical personnel performing the medical procedures. Drape 110 thus maintains a sterile field and allows for heating or cooling a patient.

Figure 3:
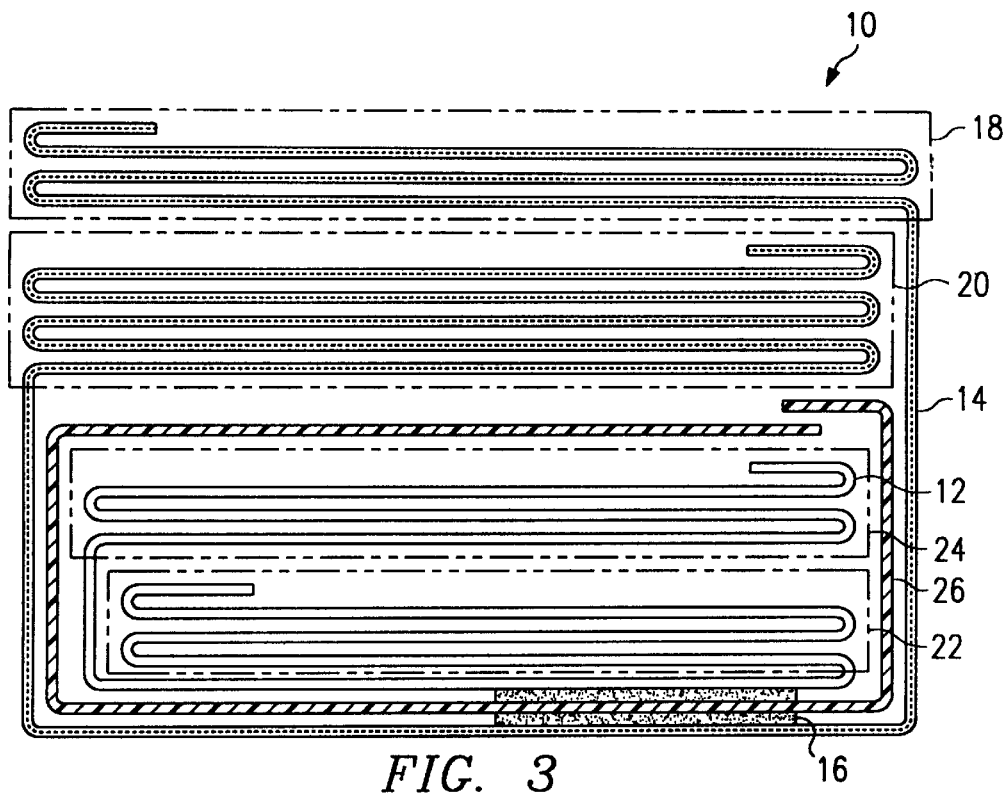
FIG. 3 depicts a sterile surgical-thermal drape showing folding, attachments, and barrier in accordance with teachings of the present invention.

FIG. 3 illustrates an alternate embodiment of sterile surgical-thermal drape 10 after folding embodying concepts of the present invention. Drape 10 in FIG. 3 includes barrier 26 that is used to help maintain the sterility of sterile surgical drape 12. Thermal head section 18 and thermal feet section 20 are externally configured as shown. Surgical drape head section 22 and surgical drape feet section 24 are internally configured as shown, enclosed by flexible thermal device 14. In addition, barrier 26 attaches by connection 16 between sterile surgical drape 12 and flexible thermal device 14. Barrier 26 may be made of many materials that act as a barrier to moisture, bacteria, and viruses, such as, for example, a thermoplastic film. Barrier 26 can either be folded around sterile surgical drape 12 or it may encase sterile surgical drape 12 and be hermetically sealed by many appropriate methods, including, but not limited to, welding, laser welding, adhesive attachment, and heat sealing. In operation, barrier 26 remains sealed until sterile surgical drape 12 is used.

Figure 4A:
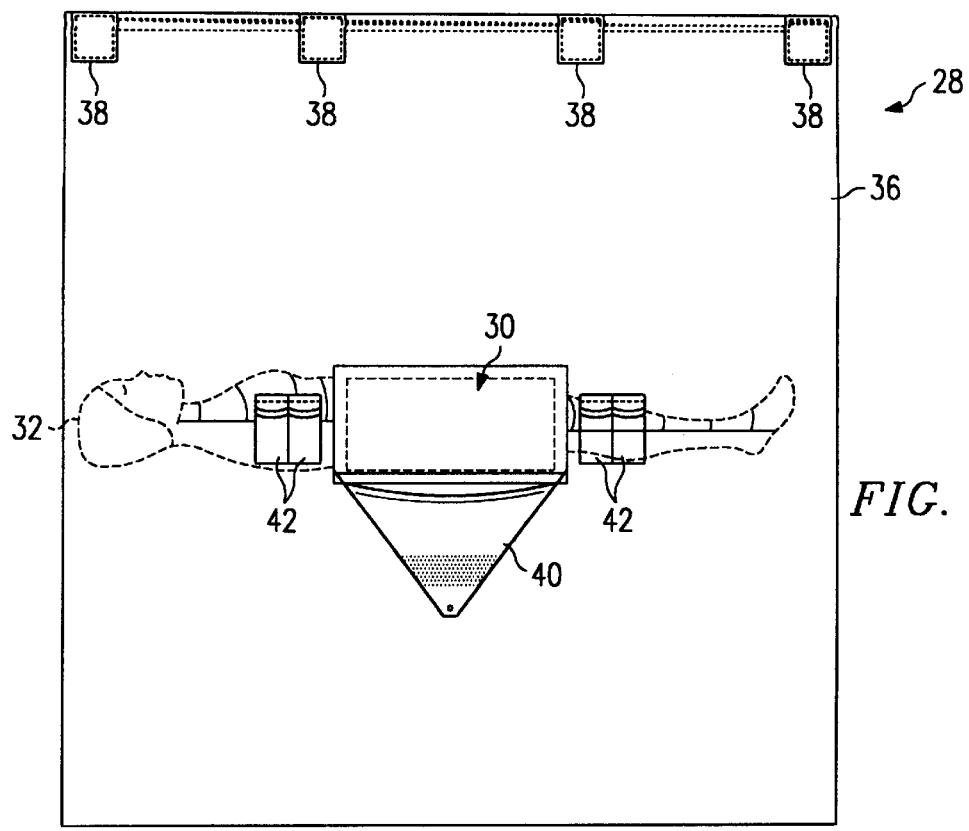
FIGS. 4A and 4B illustrate the use of a sterile surgical-thermal drape with an incise of the present invention.
Figure 4B:
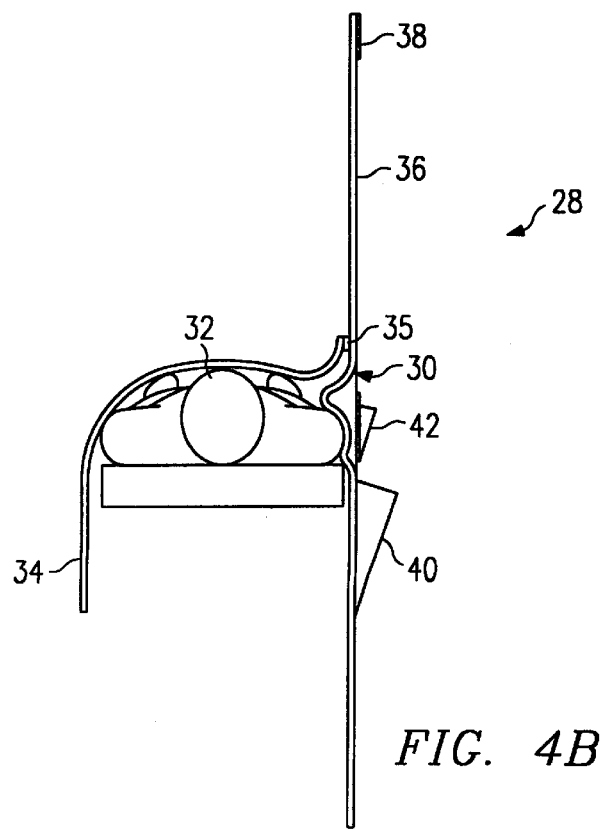

FIGS. 4A and 4B illustrate the use of sterile surgical-thermal drape 28 having fenestration/incise 30 in accordance with teachings of the present invention. As shown in FIG. 4A, fenestration/incise 30 is an area in sterile surgical-thermal drape 28 that allows medical personnel to access patient 32 while maintaining the integrity of a sterile field. Fenestration/incise 30 may be of many predetermined sizes and may be in many predetermined locations in drape 28, such that sterile surgical-thermal drape 28 can be used in connection with many medical procedures. As shown in FIG. 4A, fenestration/incise 30 is configured in drape 28 for use in hip surgery on patient 32. A sterile adhesive may be applied around the periphery of fenestration/incise 30 to secure the location of fenestration/incise 30 on patient 32.

FIG. 4B shows an alternate view of the use of sterile surgical-thermal drape 28 in FIG. 4A looking toward the head of patient 32. Drape 28 includes flexible thermal device 34 attached to sterile surgical drape 36 along a line that is parallel with patient 32. The location of fenestration/incise 30 is indicated in FIG. 4B, but fenestration/incise 30 is not explicitly shown in FIG. 4B.

In operation, sterile surgical-thermal drape 28 is suspended from overhead and adjacent to patient 32 by hanging supports 38 as shown in FIGS. 4A and 4B. Sterile surgical drape 36 hangs vertically, and flexible thermal device 34 couples to drape 36 along connection 35 that is parallel with patient 32. Flexible thermal device 34 is draped over patient 32. Fenestration/incise 30 is placed adjacent to the area to which access is required during surgery, i.e., the hip of patient 32. Adhesive may be used to attach incise 30 to a specific location on patient 32. If fenestration/incise 30 is an incise, medical personnel may remove by cutting any desired sections of fenestration/incise 30. Flexible thermal device 34 does not extend into the area defined by incise 30.

As shown in FIGS. 4A and 4B fluid pocket 40 may also be provided with drape 28 to catch any fluids that pass through fenestration/incise 30. Drape 28 may also include surgical instrument pockets 42 to hold sterile surgical instruments or devices that are required to perform the surgical procedures.

Figure 5:
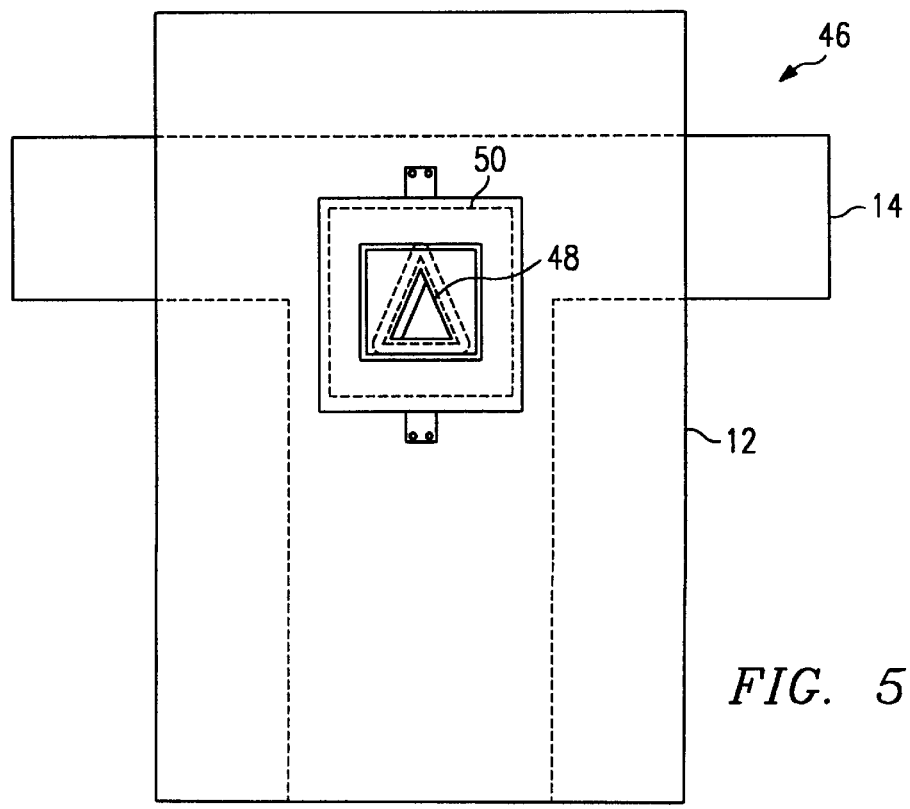
FIG. 5 shows a sterile surgical-thermal drape with a fenestration suitable for use when performing a cesarean section embodying concepts of the present invention.

FIG. 5 shows sterile surgical-thermal drape 46 embodying concepts of the present invention that may be used when performing a cesarean section birth procedure on a patient (not explicitly shown). Drape 46 includes flexible sterile surgical drape 12 and flexible thermal device 14. Fenestration/incise 48 in sterile surgical drape 12 is located in the area that the cesarean section is to be performed. Adhesive may be applied about the periphery of fenestration/incise 48 to secure surgical-thermal drape 46 to the patient (not explicitly shown).

Fluid pocket 50 is used to catch any fluids that pass through fenestration/incise 48. Flexible thermal device 14 extends over the areas shown in FIG. 5 to provide heating or cooling to a patient, but does not extend over the area defined by fenestration/incise 48. Sterile surgical-thermal drape 46 in FIG. 5 provides for appropriate heating or cooling of a patient while maintaining a sterile field. As previously noted, one skilled in the art will recognize that sterile surgical-thermal drape 46 may incorporate features of drape 110, with sterile surgical surface 112 and thermal surface 114 forming coolant passageways or enclosing active thermal elements, without departing from the scope and spirit of the present invention.

Figure 6:
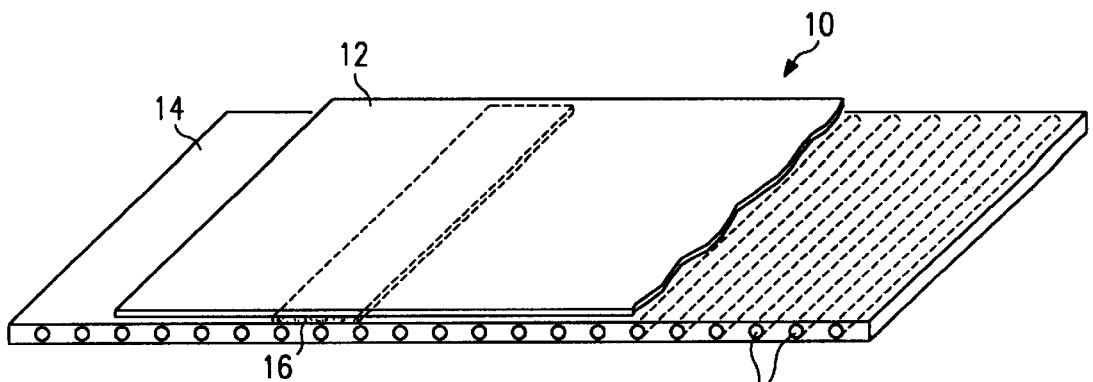
FIG. 6 illustrates a sterile surgical-thermal drape in accordance with the present invention having conducting passageways for carrying a fluid.

FIG. 6 illustrates another embodiment of the present invention and shows sterile surgical-thermal drape 10 having conducting passageways 54 in flexible thermal device 14 for carrying a fluid. Conducting passageways 54 may be formed in flexible thermal device 14 by many appropriate techniques, including, but not limited to, welding or glueing of individual laminae of flexible thermal device 14, extrusions within flexible thermal device 14, and adhesion to flexible thermal device 14. Additionally, fenestrations like those shown in FIGS. 4A, 4B, and 5 may be provided in drape 10 of FIG. 6.

In operation of surgical-thermal device 10 in FIG. 6, a manifold (not explicitly shown) is connected to a coolant/heating fluid circulation path (not explicitly shown) and to conducting passageways 54 in flexible thermal device 14. Alternatively, passageways 54 may be formed as a series of connected passages having a limited number of inputs and outputs. A coolant or heating fluid may be circulated through conducting passageways 54, thus providing cooling or heating to a patient. The fluid used in thermal device 14 may be either a liquid or a gas. As previously noted, one skilled in the art will recognize that the embodiment of sterile surgical-thermal drape 10 shown in FIG. 6 may also incorporate features of drape 110, with sterile surgical surface 112 and thermal surface 114 forming coolant passageways or enclosing active thermal elements, without departing from the scope and spirit of the present invention.

Figure 7:
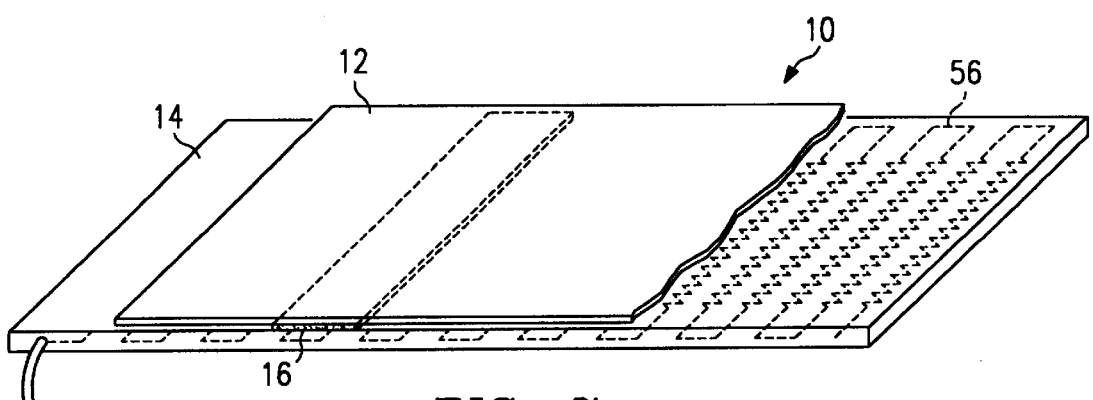
FIG. 7 shows a sterile surgical-thermal drape in accordance with the present invention having resistive heating elements.

FIG. 7 shows another embodiment of sterile surgical-thermal drape 10 of the present invention having resistive heating elements 56. Drape 10 in FIG. 7 includes sterile surgical drape 12, flexible thermal device 14, and connection 16. Resistive heating elements 56 may be fabricated from many appropriate materials. Resistive heating elements 56 are enclosed within flexible thermal device 14 by many appropriate methods, including, but not limited to, extrusion within flexible thermal device 14 and adhesion to flexible thermal device 14.

In operation of drape 10 in FIG. 7, power cord 58 couples to an appropriate power source to provide electrical energy to resistive heating elements 56. The power source may provide alternating or direct current power at many appropriate voltages and frequencies. Applying current to resistive heating elements 56 causes heat to be generated, thus providing heating to a patient. It is noted that thermoelectric elements may also be used in lieu of resistive heating elements 56, such that sterile surgical-thermal drape 10 may be used to provide cooling as well as heating to a patient. As previously noted, one skilled in the art will recognize that the embodiment of sterile surgical-thermal drape 10 shown in FIG. 7 may incorporate features of drape 110, with sterile surgical surface 112 and thermal surface 114 forming coolant passageways or enclosing active thermal elements, without departing from the scope and spirit of the present invention.

Figure 8:
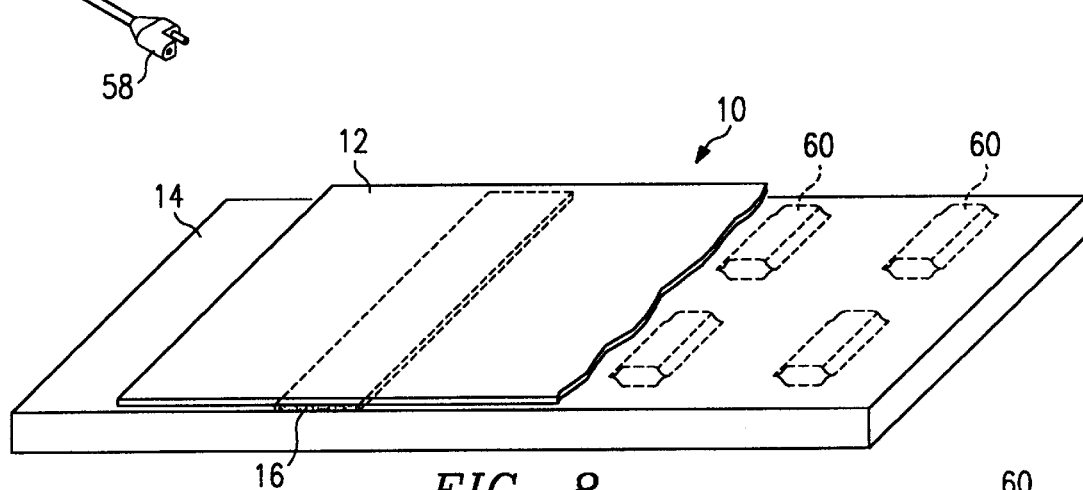
FIGS. 8 and 8A illustrate a sterile surgical-thermal drape in accordance with the present invention having thermal producing manipulably rupturable chambers.
Figure 8A:
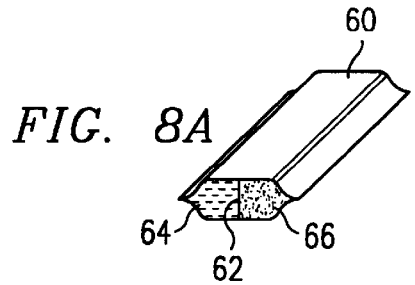

FIGS. 8 and 8A illustrate another embodiment of sterile surgical-thermal drape 10 having manipulably rupturable chambers 60. Drape 10 in FIG. 8 includes sterile surgical drape 12, flexible thermal device 14, and connection 16. Manipulably rupturable chambers 60 may be formed by many appropriate means, including, but not limited to, welding or glueing of individual laminae of flexible thermal device 14, extrusion within flexible thermal device 14, and adhesion to flexible thermal device 14.

As shown in FIG. 8A, manipulably rupturable chamber 60 includes manipulably rupturable membrane 62 and chemical reactants 64 and 66. Chemical reactants 64 and 66 create an exothermic or endothermic chemical reaction when mixed, such that rupturing manipulably rupturable membrane 62 causes chemical reactants 64 and 66 to mix and either generate (exothermic) or absorb (endothermic) heat.

In operation of drape 10 in FIGS. 8 and 8A, manipulably rupturable chamber 60 in flexible thermal device 14 of drape 10 is compressed or agitated until manipulably rupturable membrane 62 is ruptured, thus causing chemical reactants 64 and 66 to mix. After chemical reactants 64 and 66 mix, they either generate or absorb heat, thus heating or cooling a patient. As previously noted, one skilled in the art will recognize that the embodiment of sterile surgical-thermal drape 10 shown in FIG. 8 may incorporate features of drape 110, with sterile surgical surface 112 and thermal surface 114 forming coolant passageways or enclosing active thermal elements, without departing from the scope and spirit of the present invention.

The present invention thus provides a device and method that may be used to maintain a sterile surgical field while providing sufficient heat to a patient to prevent the onset of hypothermia. A device incorporating concepts of the present invention may be used to controllably provide heat to a patient undergoing surgery while maintaining the sterile environment needed to safely perform surgery. A method incorporating concepts of the present invention provides a surgical-thermal draping system that maintains the sterility of the surgical drape while allowing operating room personnel to handle and prepare the surgical-thermal draping system for use in surgery.

Although the present invention has been described in detail, it should be understood that various changes, substitutions, and alterations can be made hereto without departing from the spirit and scope of the invention as defined by the appended claims.

What is claimed is:

1. A sterile surgical-thermal drape comprising:
    a sterile surgical drape for use during surgery operable to maintain a sterile field during surgical procedures;
    a thermal device attached to the sterile surgical drape configured to regulate a body temperature of a patient during a surgical procedure using an active thermal medium; and
    a removable barrier attached between the sterile surgical drape and the thermal device and enclosing the sterile surgical drape for maintaining a sterility of the sterile surgical drape.

2. The sterile surgical-thermal drape of claim 1 wherein the sterile surgical drape further comprises one of a fenestration and an incise for exposing a portion of a body of the patient.

3. The sterile surgical-thermal drape of claim 1 wherein the thermal device comprises an insulator.

4. The sterile surgical-thermal drape of claim 1 wherein the sterile surgical drape is folded into a head section and a foot section.

5. The sterile surgical-thermal drape of claim 1, wherein the thermal device is folded into a head section and a foot section.

6. The sterile surgical-thermal drape of claim 1 wherein the sterile surgical drape further comprises a support for suspending the sterile surgical drape above the patient.

7. The sterile surgical-thermal drape of claim 1 wherein the sterile surgical drape further comprises at least one of a fluid pocket and instrument pocket.

8. A sterile surgical-thermal drape comprising:
    a sterile surgical drape for use during surgery operable to maintain a sterile field during surgical procedures;
    a thermal device attached to the sterile surgical drape configured to regulate a body temperature of a patient during a surgical procedure using an active thermal medium; and
    wherein the thermal device further comprises a passageway for circulating a fluid.

9. The sterile surgical-thermal drape of claim 8 wherein the thermal device is coupled to the sterile surgical drape to form a passageway for circulating a fluid.

10. The sterile surgical-thermal drape of claim 8 further comprising:
    a removable barrier attached between the sterile surgical drape and the thermal device and enclosing the sterile surgical drape for maintaining a sterility of the sterile surgical drape;

wherein the sterile surgical drape is folded into a head section and a foot section; and wherein the thermal device is folded into a head section and a foot section.

11. A sterile surgical-thermal drape comprising:

a sterile surgical drape for use during surgery operable to maintain a sterile field during surgical procedures;

a thermal device attached to the sterile surgical drape configured to regulate a body temperature of a patient during a surgical procedure using an active thermal medium; and wherein the thermal device further comprises an electrical heating element.

12. A sterile surgical-thermal drape comprising:

a sterile surgical drape for use during surgery, operable to maintain a sterile field during surgical procedures, and wherein the sterile surgical drape is folded into a head section and a foot section;

a thermal device attached to the sterile surgical drape operable to regulate a body temperature of a patient during a surgical procedure using an active thermal medium, and wherein the thermal device is folded into a head section and a foot section;

a removable barrier attached between the sterile surgical drape and the thermal device and enclosing the sterile surgical drape for maintaining a sterility of the sterile surgical drape; and wherein the sterile surgical drape further comprises one of a fenestration and an incise for exposing a portion of a body of the patient.

13. The sterile surgical-thermal drape of claim 12 wherein the thermal device comprises an insulator.

14. The sterile surgical-thermal drape of claim 12 wherein the thermal device further comprises a passageway for carrying a fluid.

15. The sterile surgical-thermal drape of claim 12 wherein the sterile surgical drape is coupled to the thermal device to form a passageway for conducting a fluid.

16. The sterile surgical-thermal drape of claim 12 wherein the thermal device further comprises a manipulably rupturable compartment containing one of heat-generating and heat-absorbing chemical reactants.

17. The sterile surgical-thermal drape of claim 12 wherein a manipulably rupturable compartment containing one of heat-generating and heat-absorbing chemical reactants is contained between the thermal device and the sterile surgical drape.

18. The sterile surgical-thermal drape of claim 12 wherein the thermal device further comprises an electrical heating element.

19. The sterile surgical-thermal drape of claim 12 wherein an electrical heating element is contained between the thermal device and the sterile surgical drape.

20. The sterile surgical-thermal drape of claim 12 wherein the sterile surgical drape further comprises a support for suspending the sterile surgical drape above the patient.

21. The sterile surgical-thermal drape of claim 12 wherein the sterile surgical drape further comprises at least one of a fluid pocket and instrument pocket.

22. A sterile surgical-thermal drape comprising:

a sterile surgical surface for use during surgery, operable to maintain a sterile field during surgical procedures;

a thermal surface coupled to the sterile surgical surface so as to form a compartment between the sterile surgical surface and the thermal surface;

wherein the sterile surgical surface and the thermal surface are operable to be used simultaneously during a surgical procedure; and wherein the compartment is formed as a passageway for circulating a fluid through the sterile surgical-thermal drape for regulating a body temperature of a patient.

23. The sterile surgical-thermal drape of claim 22 further comprising one of a fenestration and an incise for exposing a portion of the patient's body.

24. The sterile surgical-thermal drape of claim 22 wherein the sterile surgical surface and the thermal surface are coupled to one another through one of sonic welding, laser welding, adhesive attachment, heat sealing, hook and loop systems, plastic fixtures, and zippers.

25. The sterile surgical-thermal drape of claim 22 wherein the sterile surgical surface and the thermal surface are formed of the same material.

26. A sterile surgical-thermal drape comprising:

a sterile surgical surface for use during surgery, operable to maintain a sterile field during surgical procedures;

a thermal surface coupled to the sterile surgical surface so as to form a compartment between the sterile surgical surface and the thermal surface;

wherein the sterile surgical surface and the thermal surface are operable to be used simultaneously during a surgical procedure; and an electrical heating element, wherein the electrical heating element is placed in the compartment formed between the sterile surgical surface and the thermal surface.

* * * * *